United States Patent [19]

Schmidtz et al.

[11] Patent Number: 4,902,279
[45] Date of Patent: Feb. 20, 1990

[54] LIQUID MEDICAMENT SAFETY INJECTOR

[75] Inventors: William B. Schmidtz; William L. Schmitz, both of Hemet, Calif.

[73] Assignee: Autoject Systems Inc., Hemet, Calif.

[21] Appl. No.: 254,262

[22] Filed: Oct. 5, 1988

[51] Int. Cl.$^4$ .............................................. A61M 5/20
[52] U.S. Cl. .................................. 604/134; 604/137; 604/135
[58] Field of Search .................... 604/131, 134–137

[56] References Cited

U.S. PATENT DOCUMENTS

| | | |
|---|---|---|
| 3,064,650 | 11/1962 | Lewis . |
| 3,494,358 | 2/1970 | Fehlis . |
| 3,702,608 | 11/1972 | Tibbs . |
| 3,712,301 | 1/1973 | Sarnoff . |
| 3,792,489 | 3/1974 | Sarnoff . |
| 3,880,163 | 4/1975 | Ritterskamp ................ 128/218 F |
| 3,882,863 | 5/1975 | Sarnoff . |
| 4,194,505 | 3/1980 | Schmitz ...................... 128/218 D |
| 4,316,463 | 2/1982 | Schmitz ...................... 128/215 F |
| 4,413,991 | 11/1983 | Schmitz ...................... 604/191 |
| 4,578,064 | 3/1986 | Sarnoff et al. ............... 604/137 |
| 4,795,433 | 1/1989 | Sarnoff ........................ 604/136 |
| 4,822,340 | 4/1989 | Kamstra ...................... 604/135 |

OTHER PUBLICATIONS

"Introducing JECT AID TM Automatic Injector", brochure, Autoject Systems, Inc., Hemet, Calif. 1 p.; no date.

Autoject Preliminary Operating Instructions; Owen Mumford Limited: no date.

Insulin Therapy at Its Simplest advertisement; Squibb—Novo, Inc.; Jul. 1988.

*Primary Examiner*—J. L. Kruter
*Attorney, Agent, or Firm*—Sheldon & Mak

[57] ABSTRACT

A safety injector, primarily for self-administered medicaments, is adapted to hold a charged hypodermic syringe and its needle with the needle in a protected retracted position. When a trigger member of the injector is pressed against the skin of the patient, the needle is exposed for producing shallow penetration of the skin, then a plunger actuator is released for producing a forward movement of the syringe a limited distance to cause full penetration by the needle and a coordinated forward movement of the syringe plunger to force medicament from the syringe through the needle in a "tracked injection." A safety mechanism prevents release of the plunger actuator unless the syringe is fully seated within the injector.

31 Claims, 2 Drawing Sheets

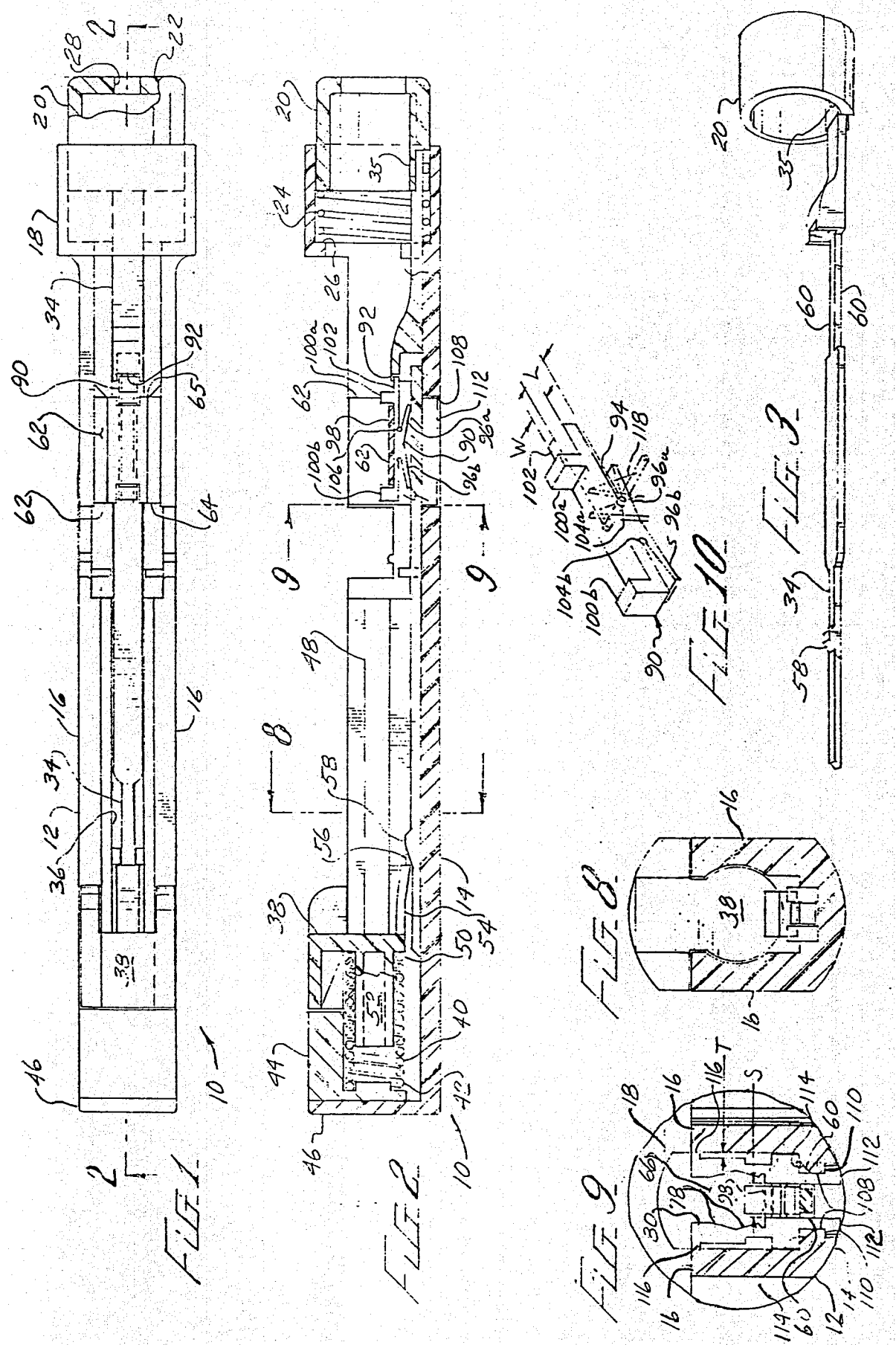

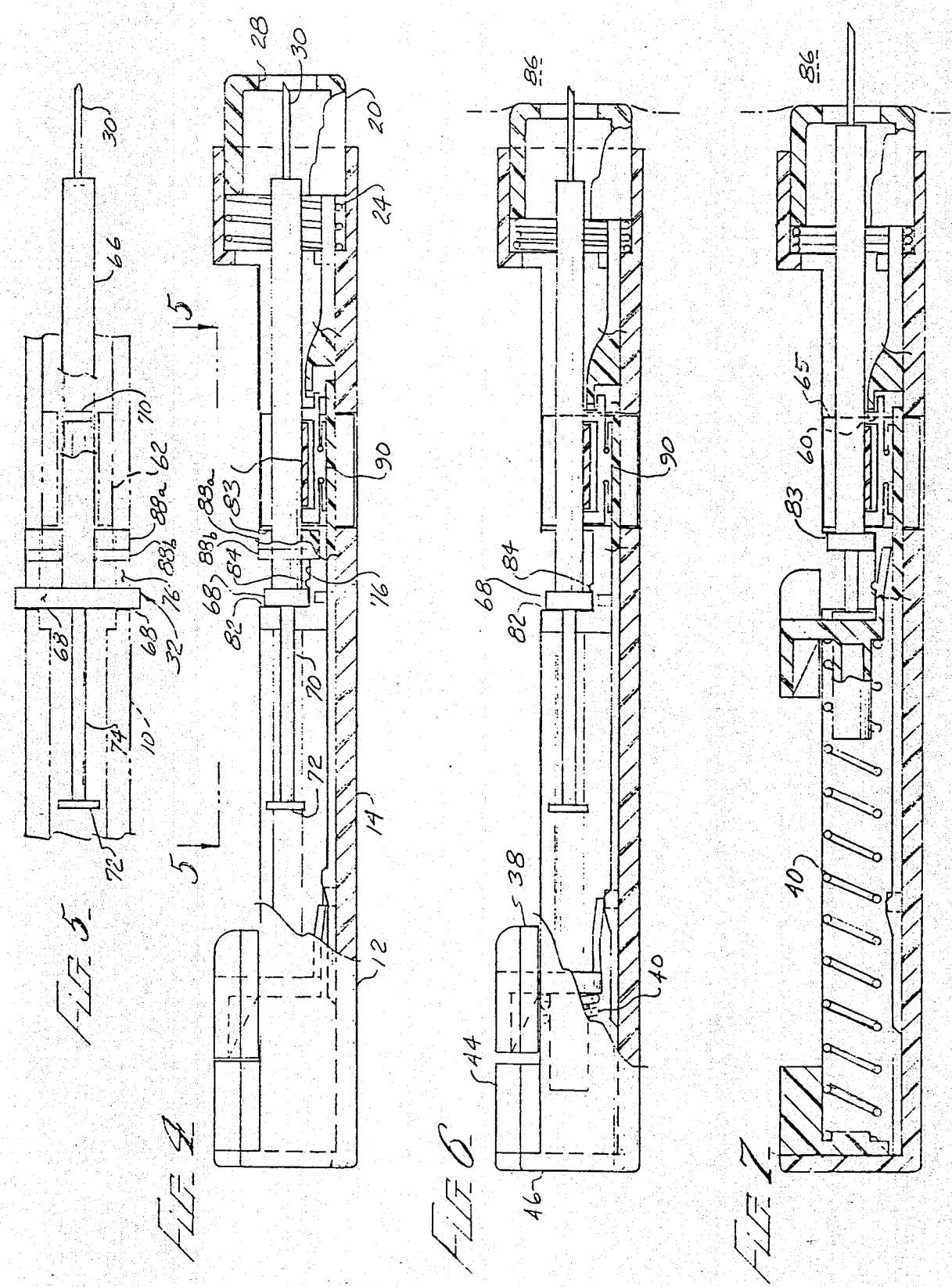

LIQUID MEDICAMENT SAFETY INJECTOR

BACKGROUND

The present invention is related to mechanisms for causing the needles on hypodermic syringes to penetrate the flesh and the plungers of the syringes to expel medicaments therefrom and through the needles into the flesh. While the invention is useful to physicians, paramedics, nurses or the like, it is particularly useful to patients who are required frequently to self-administer medicaments such as insulin in cases of diabetes.

Injector devices for facilitating hypodermic injections are known, both for medicament ampules that are furnished with the injector device, and for conventional hypodermic syringes that are operated by the device. In the case of injection from self-contained ampules, see, for example, U.S. Pat. Nos. 4,194,505, 4,316,463, and 4,413,991 to the present inventors, and U.S. Pat. No. 3,712,301 to Sarnoff. For injection from conventional syringes, see U.S. Pat. Nos. 4,494,358 to Fehlis, 3,702,608 to Tibbs, and 3,880,163 to Ritterskamp.

It is also known to provide a "tracked" injection wherein the medicament is caused to issue from the needle during movement of the needle into the patient's flesh for preventing tissue damage that would otherwise be caused by a "balloon" injection, wherein substantially all of the medicament is deposited after the needle reaches maximum penetration.

In clinical and home use applications such as for insulin injections, it is desireable to have a re-useable injector that incorporates a conventional syringe or the like for avoiding costs associated with discarding the ampule-type injectors after a single use. However, the injectors for conventional hypodermic syringes have other problems. For example, they are unreliable for accurate penetration and dosage because they are subject to operation with the syringe not properly seated in the device. Also, they are subject to inaccurate dosage due to loss of a portion of the medicament from the syringe prior to a necessary depth of needle penetration into the flesh. Moreover, they are subject to inadvertent premature actuation during attempts to engage the syringe with the injector device, consequently subjecting those nearby to possible injury.

A further problem with syringe injectors is that in case of a faulty injection, analysis of causation is clouded by the possibility of injector tampering, especially when the injector can be easily disassembled and improperly assembled by the user.

Thus there is a need for an injector device for a hypodermic syringe that reliably and safely facilitates administration of a precise medicament dosage without excessive tissue damage.

SUMMARY

The present invention is directed to a safety injector for conventional hypodermic syringes that meets this need. The injector includes an elongated body for receiving a syringe having a cylindrical barrel having a lateral projection thereon, a hypodermic needle in fluid communication with an end of the barrel, a plunger in the barrel and extending from an opposite end thereof for expelling fluid medicament from the syringe; a trigger member on the body and having a trigger surface rearwardly movable from an extended position toward the body in response to pressure from the flesh of a user, receiver means for holding the syringe axially aligned with the body, stop means for limiting movement of the syringe in the body from a first position forwardly to a second position, the needle being located behind the trigger surface in the first position of the syringe when trigger member is extended, the needle projecting beyond the trigger surface for piercing the flesh of a user when the syringe is in the second position; actuator means for forwardly moving the plunger; catch means for preventing the actuator means, release means connected to the trigger member for releasing the catch means, whereby the actuator moves the plunger forwardly in the barrel, the syringe being moved from the first position to the second position; and safety latch means for preventing the release means except when the syringe is fully seated in the receiver means. Thus the injector can be safely handled in a cocked position in the absence of the syringe without risking inadvertent operation of the actuator means that might otherwise be injurious to someone nearby. Further, the cocked injector is secured by the safety latch means from inadvertent operation of the actuator during insertion of the syringe until the syringe is fully seated in the receiver means, providing further protection for a user of the injector in addition to preventing inadvertent expulsion of fluid from the syringe that might otherwise result from operation of the actuator means during insertion of the syringe into the injector.

Preferably the trigger member is rearwardly movable to a stop position wherein the needle projects from about 0.09 inch to about 0.11 inch beyond the trigger surface when the syringe is in the first position for producing shallow penetration by the needle prior to injection of the medicament. The trigger surface can have an area of about 0.4 square inch, the trigger member activating the release means in response to a force of about 2.5 lb. from the skin pressure.

The receiver means can frictionally limit the forward movement of the syringe by a frictional resistance that is greater than a plunger frictional resistance of the syringe to forward movement of the plunger within the barrel, thus producing a tracked injection by coordinating the forward movements of the plunger and the barrel, a substantial portion of the fluid being deposited along and ahead of the needle during forward movement of the needle into the flesh. For a syringe having a capacity of about 0.5 cc and wherein the frictional resistance is about 0.5 lb., the frictional resistance of the receiver means to the forward movement of the syringe is preferably from about 2 to about 4 lbs. Further, the actuator means can be biased from about 1.5 lb. to about 4.5 lb. toward the forward end of the body. Preferably the bias of the actuator means is not more than about 3.5 lb. for providing a desired level of brain-wave cancellation upon impact of the actuator means against the plunger.

The safety latch means can include a movable contact member, means for guiding the contact member between a lock position and an armed position, the contact member being biased toward the lock position, the contact member moving to the armed position in response to seating of the syringe into the receiver means, and means connected to the contact member for preventing movement of the trigger member from the extended position when the contact member is not in the armed position. The receiver means can include a guide member having a cavity, the cavity having a lateral opening for radial movement of the barrel into the cavity, thereby releasably holding the barrel of the syringe, the contact member of the safety latch means preferably projecting into the cavity in the lock position.

In a further aspect of the invention, the actuator means, the catch means, the release means, and the safety latch means are each retained in operative relation to the body by the receiver means being fixedly attached to the body by means of interlocking connection therewith for facilitating assembly of the apparatus. The connection of the receiver means to the body can be by a pair of finger members of the receiver means outwardly engaging corresponding shoulder surfaces of the body, separation of the finger members from the body requiring simultaneous deformation of both finger members at at least two positions along each of the finger members, the finger members being formed such that localized deflection of the finger members does not bring about release of the receiver means from the body. Thus the present invention provides a low cost, relatively tamper-proof assembly that is disassemblable without damage to its components only when the finger members of the receiver means are each displaced relative to the shoulder surface at at least two independently displaceable locations along each of the finger members. The injector is thus resistant to unauthorized disassembly. Moreover in case of tampering by such unauthorized disassembly, detection of such tampering is facilitated by the claimed configuration wherein proper disassembly may be effected without further damage to components of the injector.

DRAWINGS

These and other features, aspects, and advantages of the present invention will become better understood with reference to the following description, appended claims, and accompanying drawings where:

FIG. 1 is a fragmentary sectional plan view of a safety medicament injector for hypodermic syringes according to the present invention;

FIG. 2 is a fragmentary sectional elevational view of the injector of FIG. 1 on line 2—2 of FIG. 1;

FIG. 3 is an oblique elevational perspective view of a trigger component of the injector of FIG. 1;

FIG. 4 is a fragmentary sectional elevational view as in FIG. 2, showing the injector of FIG. 1 with a conventional hypodermic needle seated therein;

FIG. 5 is a fragmentary plan view of the injector of FIG. 1 on line 5—5 of FIG. 4;

FIG. 6 is a fragmentary sectional elevational view as in FIG. 4, showing the injector in a partially triggered position;

FIG. 7 is a fragmentary sectional elevational view as in FIG. 4 showing the injector at the end of an injection cycle;

FIG. 8 is a fragmentary sectional elevational view of the injector of FIG.1 on line 8—8 of FIG. 2

FIG. 9 is a fragmentary sectional elevational view of the injector of FIG. 1. on line 9-9 of FIG. 1; and FIG. 10 is an oblique perspective elevational view of a safety catch component of the injector of FIG. 1 within region 10 of FIG. 1.

DESCRIPTION

The present invention is directed to a safety injector for conventional hypodermic syringes. With reference to the drawings, most particularly FIGS. 1-3 and 8-10, an injector 10 includes a body 12 having a base 14 and spaced sides 16. A front cylindrical ring portion 18 of the body 12 slidably receives a cup-shaped trigger member 20, the trigger member 20 having a protruding contact surface 22 and being biased forwardly of the body member 12 by a helical expansion trigger spring 24 that is interposed between the trigger member 20 and a shoulder 26 within the ring portion 18. An opening 28 is formed in the contact surface 22 for permitting a needle 30 of a conventional syringe 32 (shown in FIGS. 4 and 5 and further described below) to protrude the trigger member 20 as further described below.

As best shown FIGS. 2 and 3, the trigger member 20 has an elongated release element 34 extending rearwardly therefrom. The release element 34, further described below, is coupled by a boss 35 to the trigger member 20 and guided in rigid relation to the trigger member 20 by a channel 36 that is formed in the base 14 of the body 12.

A plunger actuator 38 is slidably guided between the sides 16 and biased forwardly toward the ring portion 18 by a helical expansion plunger spring 40, a rearward end 42 of the plunger spring 40 being located by an insert 44, the insert 44 being supported by a rearward end wall 46 of the body 12. As shown in FIGS. 2 and 8, each side 16 of the body 12 has an inwardly facing shallow longitudinal groove 48 formed therein for retaining in axial alignment the plunger actuator 38, the spring 40, and the insert 44, a forward portion 50 of the spring 40 being guided in axial alignment primarily by a cylindrical boss member 52 of the plunger actuator 38 that extends within the spring 40. An elastic tongue member 54 extends forwardly from the plunger actuator 38 for releasably retaining the actuator 38 in a cocked position shown in FIGS. 1 and 2 by engagement of the tongue member 54 with a pair of latch members 56 that are located on opposite sides of the channel 36.

A ramp member 58 is formed in the release element 34 for lifting the tongue member of the actuator 38 out of engagement with the latch members 56 in response to rearward movement of the trigger member 20.

Axial movement of the trigger member 20 with respect to the body 12 is limited by a pair of notches 60 that are formed in opposite sides of the release element 34 as shown in FIG. 3, each of the notches 60 being located for contacting opposite ends of a syringe guide block 62 through which the release element 34 passes, the trigger member 20 being movable between an extended position shown in FIGS. 1, 2, and 4 wherein the notches 60 are in contact with a rear surface 64 of the guide block 62, and a retracted position shown in FIG. 7 wherein the notches 60 are in contact with a front surface 65 of the block 62.

As shown in FIGS. 4 and 5, the hypodermic syringe 32 includes a cylindrical barrel 66 having a finger flange 68 extending on opposite sides thereof, the needle 30 in fluid communication with the barrel 66, a plunger 70 axially slidable in the barrel 66, the plunger 70 having an external rear end 72 on an extension 74 thereof. The syringe 32, normally charged with a desired quantity of medicament prior to being loaded into the injector 10, is received with the needle 30 proximate the opening 28 of the trigger member 20, the barrel 66 being locatingly supported by the guide block 62, the guide block 62 being fixedly connected to the body 12 as described below. The sides 16 of the body 12 each have formed therein a recess 76 for receiving the finger flange 64, the recesses 76 defining a limited range of axial movement of the syringe 32 within the guide block 62. As shown in FIG. 9, the guide block 62 forms a longitudinal cavity 78 having an upwardly open slot 80 opposite the base 14 of the body 12, the slot 80 being slightly narrower than the barrel 62 so that the syringe 32 must be snapped into place in the guide block 62. Further, the cavity 78 is formed to have a slight interference fit about the barrel 62 for permitting the axial movement of the syringe 32 only by overcoming a predetermined frictional resistance between the barrel 66 and the guide block 62.

With the syringe 32 in the position shown in FIG. 4, the finger flange 68 is located against a rear surface 82 of each recess 76 and behind a raised detent member 84 that is formed in each side 16 of the body 12 within the respective recesses 76. When the trigger member 20 is pressed against a targeted user's flesh region 86 as shown in FIG. 6, the trigger member 20 moves axially into the ring portion 18 of the body 12 against the trigger spring 24, the needle 30 slightly protruding the trigger member 20 through the opening 28 thereof for penetrating the flesh region 86. This rearward movement of the trigger member 20 causes the tongue member 54 to be lifted from its engagement with the latch member 56, thereby releasing the plunger actuator 38. Thus released, the plunger actuator 38 is driven forwardly by the plunger spring 40 until it strikes the rear end 72 of the plunger 70. The impact of the actuator 48 against the plunger 70 causes a sudden shock wave to be transmitted into the flesh region 86 by the trigger member 20, momentarily desensitizing the user's nervous system by brain wave cancellation. The impact also insures that the trigger member 20 becomes fully depressed to the retracted position shown in FIG. 7 and described above. Moreover, the impact acts to dislodge the finger flange 68 from the detent members 84, the detent members absorbing a portion of the impact and amplifying an initial spurt of the fluid medicament for opening a pathway facilitating needle travel and reducing tissue trauma as further described below.

The plunger actuator 38, after striking the rear end 72 of the plunger 70, continues toward the ring portion 18, simultaneously moving the plunger 70 forwardly in the barrel 66 and moving the barrel 66, together with the needle 30 and the finger flange 68, forwardly in the guide block until the flange 68 contacts a front surface 83 of the recesses 76 as shown in FIG. 7. This simultaneous movement results from a combination of the frictional resistance of the barrel to axial movement in the guide block 62 being greater than that of the plunger 70 in the barrel 66, and dynamic resistance to the flow of medicament from the needle 30, thereby producing a "tracked injection" whereby at least a substantial portion of the medicament is deposited along and ahead of the advancing needle 30. The tracked injection advantageously causes the elements of the flesh region 86, and especially its delicate blood vessels, to be moved apart ahead of the advancing needle 30, and lubricated by the medicament, thereby reducing tissue damage trauma that would result from cutting by the needle 30. If the plunger 70 is incompletely advanced in the barrel 66 at the conclusion of the forward movement of the barrel 66 as described above, the plunger actuator 38 continues its forward movement against the rear end 72 until such is the case, injecting the remainder of the medicament at the full depth of needle penetration.

A feature of the present invention is that the injector 10 can be provided with spacer means 88 for further limiting the travel of the barrel 66 below that which is defined by the cavities 78. The spacer means 88 can include one or more spacer members, designated 88a and 88b in FIGS. 4 and 5. By locating the spacer means 88 in the body 12 between the finger flange 68 and the front surface 83 of the recesses 76, the maximum penetration of the needle 30 into the flesh 86 is reduced from that shown in FIG. 7 by the total thickness of the spacer means 88.

Another and important feature of the present invention is that the injector 10 includes a safety catch for preventing premature release of the plunger actuator. As shown in FIGS. 1 and 2, a catch member 90 is interposed between a stop surface 92 of the release element 34 and the guide block 62 as described herein, thereby preventing movement of the trigger member 20 (and the release element 34) whenever the syringe 32 is not fully seated in the cavity 78 of the guide block 62. The catch member 90, shown more clearly in FIG. 10, is a molded plastic part including a relatively rigid, longitudinally oriented upper portion 94, and a pair of downwardly and oppositely extending spring members 96 (designated 96a and 96b) for upwardly biasing the upper portion 94 against a web member 98 of the guide block 62. A pair of upstanding lugs 100 (designated 100a and 100b) of the upper portion 94 retain the catch member 90 against axial movement relative to the guide block 62. The lug 100, together with a forward extension 102 of the upper portion 94, extends between the guide block 62 and the stop surface 92 of the release element 34, thus preventing rearward movement of the trigger member 20.

As shown in FIG. 4, when the syringe 32 is seated within the injector 10, the barrel 66 depresses the lugs 100 such that the forward extension 102 of the catch member 90 moves out of alignment with the stop surface 92 of the release element, thereby permitting the rearward movement of the trigger member 20 as shown in FIGS. 6 and 7, the stop surface 92 of the release element 34 passing above the forward extension 102 of the catch member 90.

As further shown in FIG. 10, the catch member 90 is formed with stress-relief undercuts 104 (designated 104a and 104b) between the upper portion 94 and the respective spring members 96. Also, the spring member 96a, being directly associated with the forward extension 102, is reinforced by a pin member 106 that is tightly located in the associated undercut of 104a. It has been discovered that the pin member 106 advantageously prevents long-term weakening of the catch member, such as might otherwise be caused by storage of the injector 10 with the syringe 32 received therein.

Further according to the present invention, the components of the injector 10 are assembled without conventional fasteners for providing a reliable, inexpensive, tamper resistant product that is adapted for evidence of actual tampering. As best shown in FIGS. 2 and 9, the guide block 62 extends downwardly from its web member 98 on opposite sides of the release element 34 (into the notches 60) and through an opening 108 in the base 14 of the body 12. A lower portion of the opening 108 is enlarged toward opposite sides of the body 12, forming a pair of shoulders 110, the downward extension of the guide block 62 forming a pair of hooked fingers 112 that engage the shoulders 110, thereby securing the guide block 62 in fixed relation to the body 12. A pair of upwardly inclined chamfers 114 are formed at opposite sides of the opening 108 for facilitating insertion of the guide block 62 into the body 12, the fingers 112 snapping into engagement with the shoulders 110 when the guide block 62 is fully seated therein. The fingers 112 are formed with a lower contour that is approximately flush with the bottom of the base 14 for preventing unauthorized disassembly of the guide block 62 from the body 12. The installation of the guide block 62 is the last step in assembly of the injector 10, the other parts, particularly the trigger member 20, the trigger spring 24, the release element 34, the plunger actuator 38, the plunger spring 40, the catch member, and the pin member 106, are securely locked in assembled relation to the body 12 with the guide block 62 in place.

A preferred order of assembly is to first slide the insert 44, the plunger spring 40, and the actuator 38 rearwardly from the proximate recesses 76 into engagement with the grooves 48 of the body, then slide the trigger spring 24, the release element 34 and the trigger member 20 (with the boss 35 of element 34 engaging the trigger member 20) rearwardly into the ring portion 18 of the body 12, the element 34 extending into the channel 36. The catch member 90 is separately located between the fingers 112 of the guide block 62 with the pin member 106 in place, the pin member 106 having a free length slightly greater than a spacing between the fingers 112 for temporarily holding the catch member 90 therebetween. Finally, with the plunger actuator 38 and the trigger member 20 held rearwardly against the biasing by the respective springs 40 and 24, the guide block 62 (with the catch member 90 and the pin member 106 in place) is lowered into the body 12 and snapped into the opening 108.

Disassembly is possible only by bending the fingers 112 inwardly from engagement with the shoulders 110 while upwardly urging the guide block 62 from the opening 108. Such disassembly is discouraged in that simultaneous inward movement of both fingers 112 is required, substantially along a full axial length thereof because the fingers are formed with sufficient longitudinal flexibility that full inward movement at only one location does not release the finger 112 from the entire length of the associated shoulder surface 110. Also, the inward deflection of the fingers 112 is limited by the release element 34 being located between the fingers 112. Attempts to accomplish this disassembly with ordinary tools such as a screwdriver or conventional pliers is expected to result in defacement of the body 12 and/or the fingers 112 by surface damage resulting from the tools digging into the respective parts of the injector 10. For factory disassembly, a special tool such as pliers having thin jaws that extend between the body 12 and the fingers 112 along the full length of the fingers 112 can be fabricated, such pliers not being commonly available.

The tracked injection feature of the present invention is obtained by close control of the interference fit between the cavity 78 and the barrel 66 of the syringe 32, in combination with a desired force profile of the plunger spring 40. For this purpose, the walls 16 advantageously reinforce the guide block 62 by contacting a pair of protrusions 116 that are formed on opposite sides of the guide block 62 at the tops of the respective walls 16. The reinforcement by the walls 16 can be controlled by the relatively inexpensive expedient of varying a thickness T of each protrusion 116.

In a preferred exemplary embodiment of the present invention for use with a standard ½ cc syringe, the trigger member is about 0.8 inch in diameter, having a travel of about 0.13 inch against a bias of about 0.5 lb. from the trigger spring 24, a maximum trigger force of about 2.5 lb. being required. The plunger spring 40 provides a bias of approximately 3.25 lb. against the plunger actuator 38 thereon, the bias decreasing to approximately 1.5 lb. at the position shown in FIG. 7, the actuator 38 traveling approximately 2.3 inches between the positions shown in FIGS. 4 and 7. The force required to move the plunger 70 forwardly in the barrel 66 for expelling fluid is about 0.5 lb., and the frictional force required for moving the barrel 66 forwardly in the cavity 78 is about 2.75 lb. The force required to depress the catch member 90 during insertion of the syringe barrel 66 into the cavity 78 is approximately 1 lb. The resistance of the guide block 62 to upward movement of the barrel 66 from the cavity is about 3.5 lb., about 2.5 lb. being required for removal as assisted by the approximate 1 lb. force from the catch member 90. The maximum bias provided by the plunger spring 40 for producing the tracked injection can be from about 2.5 lb. to about 4.5 lb. However, it is preferred to limit the bias to not more than about 3.5 lb. for effective brain-wave cancellation upon impact of the actuator 38 with the plunger 70.

The present invention provides a safe and convenient solution to the problem of administering injections by those not having specialized medical training. The injector 10 can easily be operated by the person receiving the injection, using only one hand, and the targeted flesh region 86 does not need to be in view. Moreover, the injection is quick and painless, and conventional aspiration of the syringe 32 is not needed.

For conventional syringes in other sizes, the present invention provides that separate embodiments of the injector 10 be made for each standard size of the syringe 32. Thus the reliability of the injector 10 is not compromised by adjustments that would otherwise be needed in adapting to different sizes of the syringe 32. The separate embodiments can be color coded for ease of identification.

The springs 24 and 40 are fabricated from a suitable spring-tempered material such as corrosion-resistant steel. The other parts of the injector 10 are preferably molded from a suitable plastic material for light weight and ease of fabrication. Suitable plastic materials for the injector 10 include ABS, polycarbonate, and acetyl. A particularly advantageous material for the pin member 106 is nylon which is commonly available for use as fishing line, approximately 0.022 inch in diameter.

In the exemplary preferred embodiment of the injector 10, the catch member 90 has a width W of 0.1 inch, the fingers 112 are spaced apart by a distance S of 0.125 inch, and the pin member 106 has a length L of 0.130 inch. Thus the catch member 90 is free to move vertically between the fingers 112, yet the member 90 is retained in place during assembly by a slight interference fit between the ends of the pin member 106 and the fingers 112. A quick and effective method for fabricating the pin member 106 without expensive tooling and set-up expense includes the steps of axially inserting a length of the 0.022 diameter material into the undercut 104a with one end of the material flush with a side of the catch member 90, then shearing the material using a pair of scissors 118, one blade of which is located against the opposite side of the catch member 90, the blade having a thickness of 0.030, the excess of the length L over the width W.

Although the present invention has been described in considerable detail with reference to certain preferred versions thereof, other versions are possible. Therefore, the spirit and scope of the appended claims should not necessarily be limited to the description of the preferred versions contained herein.

What is claimed is:

1. A hypodermic syringe safety injector apparatus for use with a conventional medical syringe comprising a cylindrical barrel having a syringe axis, a lateral projection on the barrel, a hypodermic needle carried by and in fluid connection with one end of the barrel, the needle having a tip extending a fixed distance relative to the lateral projection, a fluid expelling plunger in the barrel and having a portion extending from an opposite end of the barrel, the injector apparatus comprising:

(a) an elongated body for receiving the syringe, the body having a forward end for the needle and a rearward end for the extending portion of the plunger;

(b) a trigger member supported by the body and having a trigger surface projecting forward of the forward end of the body, the trigger member being adapted for rearward movement from an extended position relative to the body in response to pressure exerted against the trigger surface by the flesh of a patient;

(c) receiver means for holding the syringe in axial alignment with the body;

(d) stop means for limiting movement of the syringe barrel from a rearward first position to a forward second position relative to the body, the tip of the needle being located rearwardly of the trigger surface in the first position when the trigger member is in the extended position, the needle being projected beyond the trigger surface in the second position for piercing the flesh of a user;

(e) actuator means for moving the plunger in a direction toward the forward end of the body;

(f) catch means for preventing operation of the actuator means;

(g) release means activated by the trigger member for releasing the catch means, whereby the plunger is projected forwardly within the barrel and the syringe is moved from the first position to the second position in response to movement of the plunger; and (h) safety latch means for preventing operation of the release means except when the syringe is fully seated in the receiver means.

2. The apparatus of claim 1 wherein the trigger member is rearwardly movable from the extended position to a stop position relative to the body, the needle projecting from about 0.09 inch to about 0.11 inch beyond the trigger surface when the trigger surface is in the stop position and the syringe is in the first position.

3. The apparatus of claim 1 wherein the trigger surface has an area of approximately 0.4 square inch, the trigger member requiring a force of about 2.5 lb. from the skin pressure of the patient for activating the release means.

4. The apparatus of claim 1 wherein the receiver means provides a frictional resistance to the forward movement of the syringe barrel, the frictional resistance of the receiver means being greater than a plunger frictional resistance to forward movement of the plunger within the barrel, the apparatus coordinating the forward movement of the plunger in the barrel and the forward movement of the barrel in the receiver means to produce a tracked injection whereby a substantial portion of the fluid is deposited along and ahead of the needle during forward movement of the needle into the flesh.

5. The apparatus of claim 4 wherein the syringe has a capacity of approximately 0.5 cc and the plunger frictional resistance from the receiver means being from about 2 lb. to about 4 lb. during he forward movement of the syringe.

6. The apparatus of claim 5 wherein the actuator means is biased from about 1.5 lb. to about 4.5 lb. toward the forward end of the body.

7. The apparatus of claim 6 wherein the actuator means is biased to not more than about 3.5 lb.

8. The apparatus of claim 1 wherein the safety latch means comprises:

(a) a movable contact member;

(b) means for guiding the contact member from a lock position to an armed position in response to seating of the syringe into the receiver means;

(c) means for biasing the contact member toward the lock position; and (d) means operatively coupled to the contact member for preventing movement of the trigger member from the extended position when the contact member is not in the armed position.

9. The apparatus of claim 8 wherein the receiver means comprises a guide member having a cavity for releasably holding the barrel of the syringe, the cavity having a lateral opening for radial movement of the barrel into the cavity, the contact member projecting into the cavity in the lock position.

10. The apparatus of claim 1 wherein the actuator means, the catch means, the release means, and the safety latch means are each retained in operative relation to the body by the receiver means being fixedly attached to the body in an interlocking connection therewith for facilitating assembly of the apparatus.

11. The apparatus of claim 10 wherein the connection of the receiver means to the body comprises a pair of finger members of the receiver means outwardly engaging corresponding shoulder surfaces of the body, whereby separation of the finger members from the body requires simultaneous deformation of both the finger members at at least two positions along each of the finger members, the finger members each being sufficiently flexible so that deflection thereof at only one of the positions does not effect the release of the receiver means from the body.

12. A hypodermic syringe safety injector apparatus for use with a conventional medical syringe comprising a cylindrical barrel having a syringe axis, a lateral projection on the barrel, a hypodermic needle carried by and in fluid connection with one end of the barrel, the needle having a tip extending a fixed distance relative to the lateral projection, a fluid expelling plunger in the barrel and having a portion extending from an opposite end of the barrel, the injector apparatus comprising:

(a) an elongated body for receiving the syringe, the body having a forward end for the needle and a rearward end for the extending portion of the plunger;

(b) a trigger member supported by the body and having a trigger surface projecting forward of the forward end of the body, the trigger member being adapted for rearward movement from an extended position to a stop position relative to the body in response to pressure exerted against the trigger surface by the flesh of a patient;

(c) receiver means for holding the syringe in axial alignment with the body, the receiver means providing a frictional resistance to the forward movement of the syringe barrel, the frictional resistance of the receiver means being greater than a plunger frictional resistance to forward movement of the plunger within the barrel, the apparatus coordinating the forward movement of the plunger in the barrel and the forward movement of the barrel in the receiver means to produce a tracked injection whereby a substantial portion of the fluid is deposited along and ahead of the needle during forward movement of the needle into the flesh, comprising a guide member having a cavity for releasably holding the barrel of the syringe, the cavity having a lateral opening for radial movement of the barrel into the cavity;

(d) stop means for limiting movement of the syringe barrel from a rearward first position to a forward second position relative to the body, the tip of the needle being located rearwardly of the trigger surface in the first position when the trigger member is in the extended position, the needle projecting from about 0.09 inch to about 0.11 inch beyond the trigger surface when the trigger surface is in the stop position and the syringe is in the first position for piercing the flesh of a user, the needle being projected farther beyond the trigger surface in the second position;

(e) actuator means for moving the plunger in a direction toward the forward end of the body;

(f) catch means for preventing operation of the actuator means;

(g) release means activated by the trigger member for releasing the catch means, whereby the plunger is projected forwardly within the barrel and the syringe is moved from the first position to the second position in response to movement of the plunger; and (h) safety latch means for preventing operation of the release means except when the syringe is fully seated in the receiver means, comprising:
  (i) a movable contact member;
  (ii) means for guiding the contact member from a lock position to an armed position in response to seating of the syringe into the receiver means, the contact member projecting into the cavity in the lock position;
  (iii) means for biasing the contact member toward the lock position; and
  (iv) means operatively coupled to the contact member for preventing movement of the trigger member from the extended position when the contact member is not in the armed position.

13. A hypodermic syringe safety injector apparatus comprising:
(a) a medical syringe comprising a cylindrical barrel having a syringe axis, a lateral projection on the barrel, a hypodermic needle carried by and in fluid connection with one end of the barrel, the needle having a tip extending a fixed distance relative to the lateral projection, a fluid expelling plunger in the barrel and having a portion extending from an opposite end of the barrel;

(b) an elongated body for removably holding the syringe, the body having a forward end for the needle and a rearward end for the extending portion of the plunger;

(c) a trigger member supported by the body and having a trigger surface projecting forward of the forward end of the body, the trigger member being adapted for rearward movement from an extended position relative to the body in response to pressure exerted against the trigger surface by the flesh of a patient;

(d) receiver means for holding the syringe in axial alignment with the body;

(e) stop means for limiting movement of the syringe barrel from a rearward first position to a forward second position relative to the body, the tip of the needle being located rearwardly of the trigger surface in the first position when the trigger member is in the extended position, the needle being projected beyond the trigger surface in the second position for piercing the flesh of a user;

(f) actuator means for moving the plunger in a direction toward the forward end of the body;

(g) catch means for preventing operation of the actuator means;

(h) release means activated by the trigger member for releasing the catch means, whereby the plunger is projected forwardly within the barrel and the syringe is moved from the first position to the second position in response to movement of the plunger; and (i) safety latch means for preventing operation of the release means except when the syringe is fully seated in the receiver means.

14. The apparatus of claim 13 wherein the safety latch means comprises:
  (a) a movable contact member;
  (b) means for guiding the contact member from a lock position to an armed position in response to seating of the syringe into the receiver means;
  (c) means for biasing the contact member toward the lock position; and
  (d) means operatively coupled to the contact member for preventing movement of the trigger member from the extended position when the contact member is not in the armed position.

15. The apparatus of claim 14 wherein the receiver means comprises a guide member having a cavity for releasably holding the barrel of the syringe, the cavity having a lateral opening for radial movement of the barrel into the cavity, the contact member projecting into the cavity in the lock position.

16. A hypodermic syringe injector apparatus for use with a conventional medical syringe comprising a cylindrical barrel having a syringe axis, a lateral projection on the barrel, a hypodermic needle carried by and in fluid connection with one end of the barrel, the needle having a tip extending a fixed distance relative to the lateral projection, a fluid expelling plunger in the barrel and having a portion extending from an opposite end of the barrel, the injector apparatus comprising:
  (a) an elongated body for receiving the syringe, the body having a forward end for the needle and a rearward end for the extending portion of the plunger;
  (b) a trigger member supported by the body and having a trigger surface projecting forward of the forward end of the body, the trigger member being adapted for rearward movement from an extended position relative to the body in response to pressure exerted against the trigger surface by the flesh of a patient;

(c) receiver means for holding the syringe in axial alignment with the body, the receiver means providing a frictional resistance to the forward movement of the syringe barrel, the frictional resistance of the receiver means being greater than a plunger frictional resistance to forward movement of the plunger within the barrel, the apparatus coordinating the forward movement of the plunger in the barrel and the forward movement of the barrel in the receiver means to produce a tracked injection whereby a substantial portion of the fluid is deposited along and ahead of the needle during forward movement of the needle into the flesh;

(d) stop means for limiting movement of the syringe barrel from a rearward first position to a forward second position relative to the body, the tip of the needle being located rearwardly of the trigger surface in the first position when the trigger member is in the extended position, the needle being projected beyond the trigger surface in the second position for piercing the flesh of a user;

(e) actuator means for moving the plunger in a direction toward the forward end of the body;

(f) catch means for preventing operation of the actuator means; and (g) release means activated by the trigger member for releasing the catch means, whereby the plunger is projected forwardly within the barrel and the syringe is moved from the first position to the second position in response to movement of the plunger.

17. The apparatus of claim 16 wherein the trigger member is rearwardly movable from the extended position to a stop position relative to the body, the needly projecting from about 0.09 inch to about 0.11 inch beyond the trigger surface when the trigger surface is in the stop position and the syringe is in the first position.

18. The apparatus of claim 16 wherein the trigger surface has an area of approximately 0.4 square inch, the trigger member requiring a force of about 2.5 lb. from the skin pressure of the patient for activating the release means.

19. The apparatus of claim 16 wherein the frictional resistance of the receiver means is at least about five times the plunger frictional resistance.

20. The apparatus of claim 16 wherein the syringe has a capacity of approximately 0.5 cc and the plunger frictional resistance is approximately 0.5 lb., the frictional resistance from the receiver means being from about 2 lb. to about 4 lb. during the forward movement of the syringe.

21. The apparatus of claim 20 wherein the actuator means is biased from about 1.5 lb to about 4.5 lb. toward the forward end of the body.

22. The apparatus of claim 21 wherein the actuator means is biased to not more than about 3.5 lb.

23. The apparatus of claim 16 wherein the actuator means, the catch means, and the release means are each retained in operative relation to the body by the receiver means being fixedly attached to the body in an interlocking connection therewith for facilitating assembly of the apparatus.

24. The apparatus of claim 23 wherein the connection of the receiver means to the body comprises a pair of finger members of the receiver means outwardly engaging corresponding shoulder surfaces of the body, whereby separation of the finger members from the body requires simultaneous deformation of both the finger members at at least two positions along each of the finger members, the finger members each being sufficiently flexible so that deflection thereof at only one of the positions does not effect the release of the receiver means from the body.

25. A hypodermic syringe injector apparatus for use with a conventional medical syringe comprising a cylindrical barrel having a syringe axis, a lateral projection on the barrel, a hypodermic needle carried by and in fluid connection with one end of the barrel, a fluid expelling plunger in the barrel and having a portion extending from an opposite end of the barrel, the injector apparatus comprising:

(a) an elongated body for receiving the syringe, the body having a forward end for the needle and a rearward end for the extending portion of the plunger;

(b) a trigger member supported by the body and having a trigger surface projecting forward of the forward end of the body, the trigger member being adapted for rearward movement from an extended position to a stop position relative to the body in response to pressure exerted against the trigger surface by the flesh of a patient;

(c) receiver means for holding the syringe in axial alignment with the body, the receiver means providing a frictional resistance to the forward movement of the syringe barrel, the frictional resistance of the receiver means being at least about quadruple a plunger frictional resistance to forward movement of the plunger within the barrel, the apparatus coordinating the forward movement of the plunger in the barrel and the forward movement of the barrel in the receiver means to produce a tracked injection whereby a substantial portion of the fluid is deposited along and ahead of the needle during forward movement of the needle into the flesh, comprising a guide member having a cavity for releasably holding the barrel of the syringe, the cavity having a lateral opening for radial movement of the barrel into the cavity;

(d) stop means for limiting movement of the syringe barrel from a rearward first position to a forward second position relative to the body, the tip of the needle being located rearwardly of the trigger surface in the first position when the trigger member is in the extended position, the needle projecting from about 0.09 inch to about 0.11 inch beyond the trigger surface when the trigger surface is in the stop position and the syringe is in the first position for piercing the flesh of a user, the needle being projected farther beyond the trigger surface in the second position;

(e) actuator means for moving the plunger in a direction toward the forward end of the body;

(f) catch means for preventing operation of the actuator means; and (g) release means activated by the trigger member for releasing the catch means, whereby the plunger is projected forwardly within the barrel and the syringe is moved from the first position to the second position in response to movement of the plunger.

26. The apparatus of claim 25 wherein the syringe has a capacity of approximately 0.5 cc, the plunger having a frictional resistance of approximately 0.5 lb., the frictional resistance from the receiver means being from about 2 lb. to about 4 lb. during the forward movement of the syringe.

27. The apparatus of claim 26 wherein the actuator means is biased from about 1.5 lb. to about 3.5 lb. toward the forward end of the body.

28. A hypodermic syringe injector apparatus comprising:
- (a) a medical syringe comprising a cylindrical barrel having a syringe axis, a lateral projection on the barrel, a hypodermic needle carried by and in fluid connection with one end of the barrel, the needle having a tip extending a fixed distance relative to the lateral projection, a fluid expelling plunger in the barrel and having a portion extending from an opposite end of the barrel;
- (b) an elongated body for receiving the syringe, the body having a forward end for the needle and a rearward end for the extending portion of the plunger;
- (c) a trigger member supported by the body and having a trigger surface projecting forward of the forward end of the body, the trigger member being adapted for rearward movement from an extended position relative to the body in response to pressure exerted against the trigger surface by the flesh of a patient;
- (d) receiver means for holding the syringe in axial alignment with the body, the receiver means providing a frictional resistance to the forward movement of the syringe barrel, the frictional resistance of the receiver means being at least about quadruple a plunger frictional resistance to forward movement of the plunger within the barrel, the apparatus coordinating the forward movement of the plunger in the barrel and the forward movement of the barrel in the receiver means to produce a tracked injection whereby a substantial portion of the fluid is deposited along and ahead of the needle during forward movement of the needle into the flesh.
- (e) stop means for limiting movement of the syringe barrel from a rearward first position to a forward second position relative to the body, the tip of the needle being located rearwardly of the trigger surface in the first position when the trigger member is in the extended position, the needle being projected beyond the trigger surface in the second position for piercing the flesh of a user;
- (f) actuator means for moving the plunger in a direction toward the forward end of the body;
- (g) catch means for preventing operation of the actuator means; and
- (h) release means activated by the trigger member for releasing the catch means, whereby the plunger is projected forwardly within the barrel and the syringe is moved from the first position to the second position in response to movement of the plunger.

29. The apparatus of claim 28 wherein the syringe has a capacity of approximately 0.5 cc and the plunger frictional resistance is approximately 0.5 lb., the frictional resistance from the receiver means being from about 2 lb. to about 4 lb. during the forward movement of the syringe.

30. The apparatus of claim 29 wherein the actuator means is biased from about 1.5 lb. to about 4.5 lb. toward the forward end of the body.

31. The apparatus of claim 30 wherein the actuator means is biased to not more than about 3.5 lb.

* * * * *